United States Patent [19]

Kobayashi

[11] Patent Number: 4,479,116

[45] Date of Patent: Oct. 23, 1984

[54] CAPACITIVE TYPE FUEL LEVEL AND IMPURITY INDICATOR

[75] Inventor: Hiroshi Kobayashi, Yokohama, Japan

[73] Assignee: Nissan Motor Company, Ltd., Japan

[21] Appl. No.: 408,704

[22] Filed: Aug. 16, 1982

[30] Foreign Application Priority Data

Aug. 27, 1981 [JP] Japan .................. 56-133340

[51] Int. Cl.³ .................. G08B 21/00; G01F 23/26
[52] U.S. Cl. .................. 340/620; 73/304 C; 73/61.12
[58] Field of Search ........ 73/291, 304 C, 61.1 R; 340/620; 324/61 R

[56] References Cited

U.S. PATENT DOCUMENTS 4,296,630 10/1981 Jung et al. .................. 73/304
4,434,657 3/1984 Matsumura .................. 73/304 C

FOREIGN PATENT DOCUMENTS 671420 5/1952 United Kingdom .
673988 6/1952 United Kingdom .
708940 5/1954 United Kingdom .
2046918 11/1980 United Kingdom .
1578527 11/1980 United Kingdom .

OTHER PUBLICATIONS

Freeman, John D., "Capacitance Fuel Measurement For Automotive Applications", Society of Automotive Engineers, Inc., pp. 51-57 (1980).
H. F. Grave, Elektrische Messung Nicht Elektrischer Grössen S., 260-266.
Elektronik, 1957, No. 12, S. 360 bis 363.

Primary Examiner—John W. Caldwell, Sr.
Assistant Examiner—Vincent P. Kovalick
Attorney, Agent, or Firm—Lowe, King, Price & Becker

[57] ABSTRACT

A pump located within the fuel tank discharges fuel into a chamber containing a plurality of reference electrodes which determine the dielectric constant of the fuel. The output of a set of measuring electrodes is calibrated using the dielectric constant determined using the reference electrodes. The fluctuations in the capacitance developed by the reference electrodes due to momentary contact with water droplets or the like can be used to indicate an excess of the water or the like in the fuel.

11 Claims, 7 Drawing Figures

CAPACITIVE TYPE FUEL LEVEL AND IMPURITY INDICATOR

BACKGROUND OF THE INVENTION

1. Field of the Invention

The present invention relates generally to a capacitive type filling measuring apparatus for determining the quantity of fuel or other liquid medium remaining in the fuel tank of a vehicle or the like, and more specifically to an improved arrangement wherein the compensation or reference electrodes which sense the actual dielectric constant of the fuel (or liquid medium) are arranged to eliminate any erroneous indications by the apparatus due to the presence of water or other impurities in the fuel.

2. Description of the Prior Art

In previously proposed arrangements it has been proposed to place a set of reference or compensation electrodes near the bottom of a fuel tank in order to ascertain the dielectric constant of the fuel within the tank so that the output of fuel level sensing electrodes can be modified to allow for the inevitable variations in said dielectric constant of the fuel. However, such an arrangement suffers from the drawback that water or other foreign matter tends to infiltrate in between the plates or electrodes of the reference sensor causing the same to output an erroneous indication of the dielectric constant of the fuel. Water in particular is apt to stay between the plates despite the sloshing of the fuel within the tank, as water has a surface tension about three times that of gasoline. In order to remove this water (or the like) it is usually necessary to remove the reference electrodes and to clean the same using compressed air or the like. Moreover, should the fuel in the tank separate into layers such as is apt to occur when the tank is filled with so called "gasohol" (gasoline-alcohol mixture), or should an excessive amount of water collect in said tank, the output of the reference electrodes is indicative of the dielectric constant of the lower layer only and once again leads to erroneous indications of the fuel volume.

SUMMARY OF THE INVENTION

The present invention features an arrangement wherein a pump is disposed within the fuel tank itself and is arranged to discharge fuel through a conduit system including a set of reference electrodes which are arranged essentially parallel with the direction of flow. With this arrangement any water or the like which tends to collect between the plates defining the reference electrodes is soon flushed out from between the same thereby ensuring an accurate indication of the fuel dielectric constant. Further, the arrangement is able to detect via fluctuations of the capacitance developed by the reference electrodes the amount of impurities (for example water) contained in the fuel and or the seperation of "gasohol", for examples into discrete layers and to produce an alarm indicative of same.

BRIEF DESCRIPTION OF THE DRAWINGS

The features and advantages of the arrangement of the present invention will become more clearly appreciated from the following description taken in conjunction with the accompanying drawings in which.

DETAILED DESCRIPTION OF THE PREFERRED EMBODIMENTS

Figure 1:
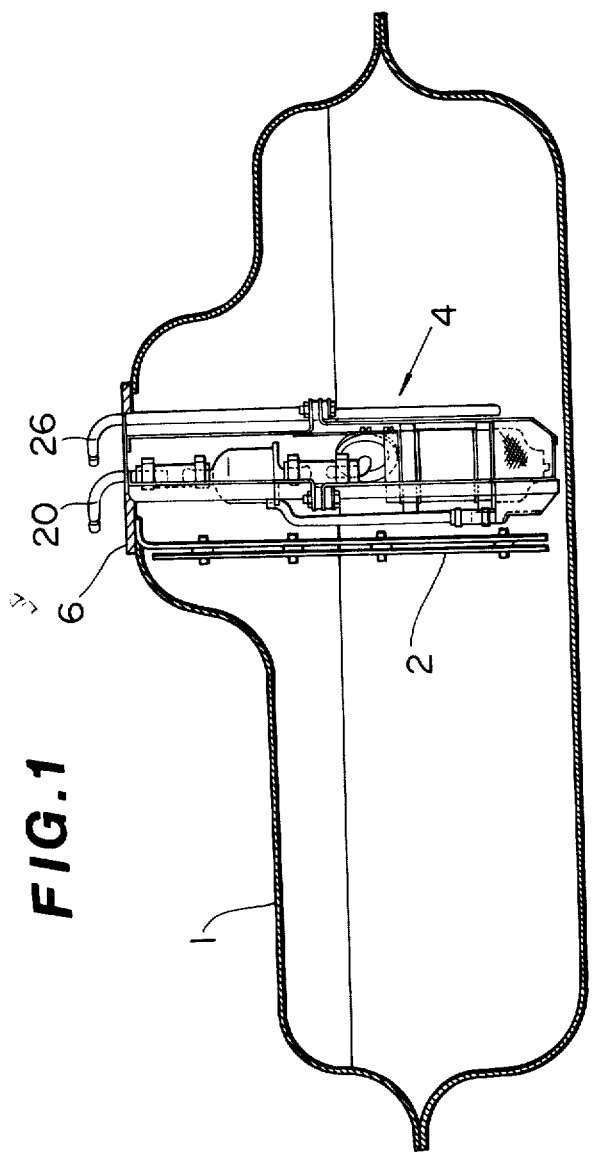
FIG. 1 is a partially sectioned view of an embodiment of the present invention.

Turning to the drawings and in particular to FIG. 1, a preferred embodiment of the present invention is shown. In this arrangement a fuel tank 1 has a set of measuring electrodes 2 mounted therein for detecting the level of the fuel. Disposed adjacent the measuring electrodes 2 is a pump and reference electrode arrangement generally denoted by the numeral 4. As shown, both the measuring electrodes 2 and the pump and reference electrode arrangement 4 are mounted on a lid 6 which is adapted to close an aperture formed in the upper portion of the fuel tank 1.

Figure 2:
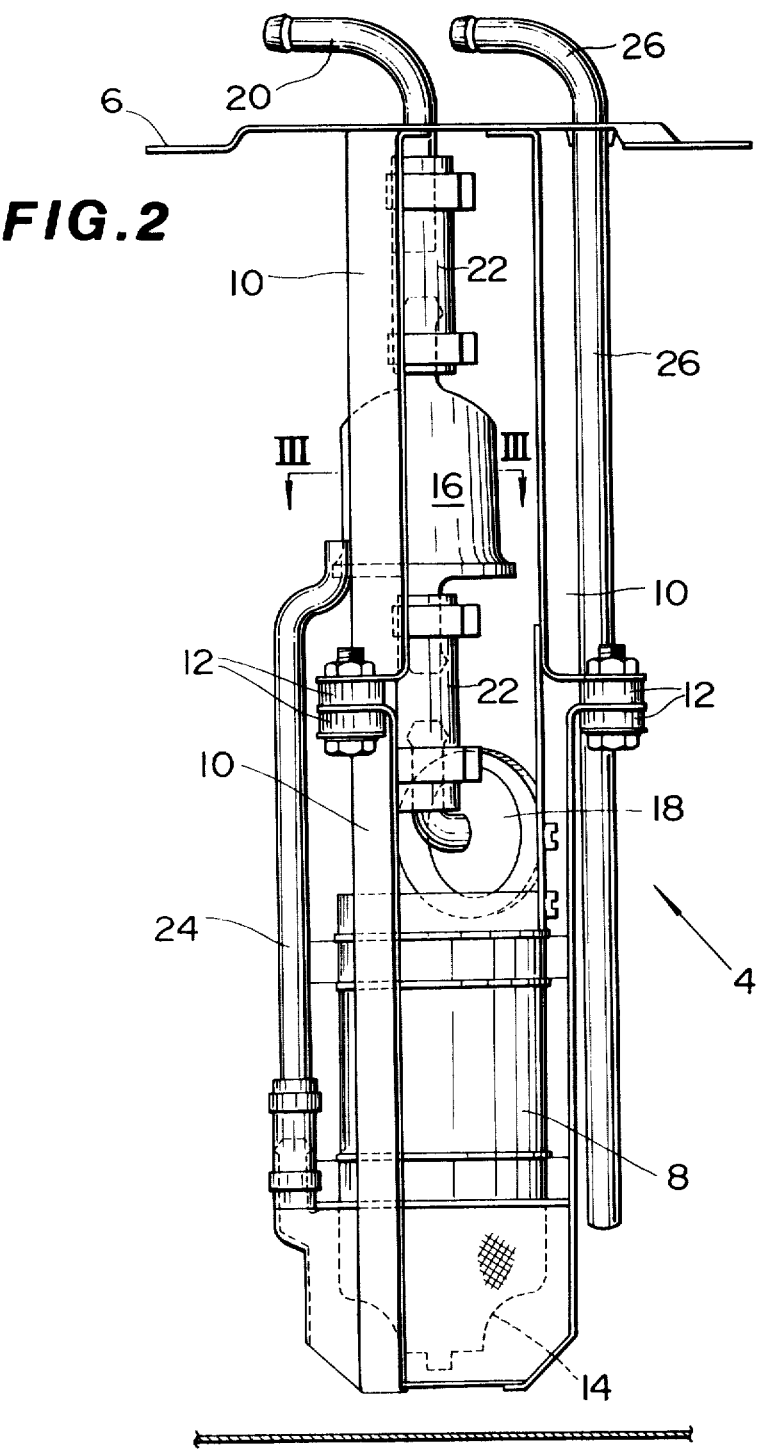
FIG. 2 is an enlarged view of the pump and reference sensor arrangement shown in FIG. 1.
Figure 3:
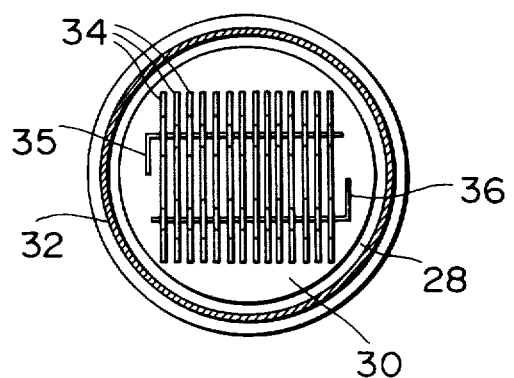
FIG. 3 is a cross sectional view taken along section line III—III of FIG. 2.

FIG. 2 is an elarged view showing the pump and reference electrode arrangement 4. In this figure a pump 8 is secured to the lid via brackets 10 and vibration insulators 12 which damp any vibrations which might tend to be transmitted to the fuel tank per se. A filter 14 is disposed about the end of the pump in which is formed the induction port thereof while the discharge port of the pump is connected to a reference electrode housing unit 16 through a pressure regulator valve 18. As shown, the housing unit 16 is connected to the pressure regulator valve 18 and the fuel discharge conduit 20 through flexible vibration damping hoses 22.

Extending from the lower end of the pump is a hose 24 for discharging bubbles and the like which might tend to be formed and tend to unwantedly enter the pump. Extending from the lid 6 down beside the pump and reference electrode arrangement 4 is a fuel return pipe 26.

Figure 4:
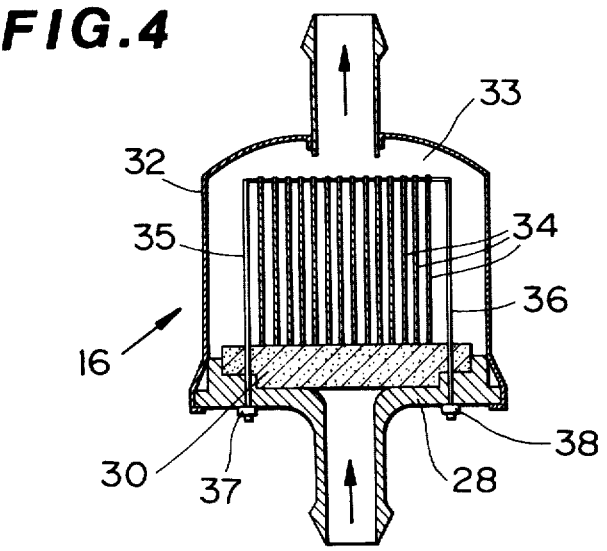
FIG. 4 is a longitudinal section of the reference electrodes and the housing unit in which they are disposed.
Figure 5:
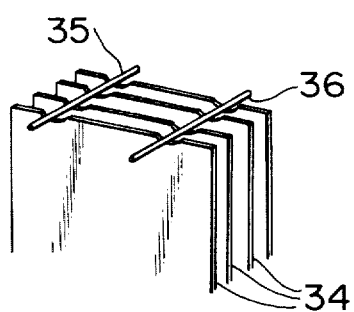
FIG. 5 is a perspective view of the reference electrodes shown in FIGS. 3 and 4.

As best seen in FIG. 4 the housing unit 16 includes a base member 28 on which a filter 30 is mounted and a bell-like member 32 which fits onto the base portion to define a chamber 33. Seated on the filter 30 which in this case is preferably a porous synthetic resin of about 200 to 500 mesh, are a plurality of parallel reference electrodes 34. Interconnecting alternate electrode plate are lead wires 35, 36. As shown these lead wires terminate in connection terminals 37, 38 formed at the bottom of the base member 28. As shown, the electrode plates 34 are arranged parallel with the direction of flow. This facilitates a "flushing" out of any water or the like which tends to accumulate therebetween.

In operation, when the pump 8 is energized, fuel is discharged therefrom through the pressure regulator valve 18 into the reference electrode housing unit 16 and thereafter to an engine or the like (not shown) via the fuel discharge conduit 20. While the pump 8 is discharging fuel, the chamber 33 of the housing unit 16 is constantly filled and the fuel forced to flow between the reference electrodes 34 which develop a capacitance $C_f$ according to the following equation:

$$C_f = E_f S_1/d_1 \cdot (n-1) \quad (1)$$

wherein $E_f$ denotes the dielectric constant of the fuel, $S_1$ the area of each of the reference plates, $d_1$ the distance between each of the plates and n the number of plates or reference electrodes.

Simultaneously, the measuring electrodes 2 develop a capacitance $C_m$ according to the following equation $$C_m = E_f S_2/S_d \cdot x + E_a \cdot S_2/S_d (1-x) \quad (2)$$

wherein $E_f$ indicates the dielectric constant of the fuel, $E_a$ the dielectric constant of air, $S_2$ the area of the electrode members, $d_2$ the spacing between the electrodes and x the proportion of the electrodes actually immersed in the fuel.

Figure 6:
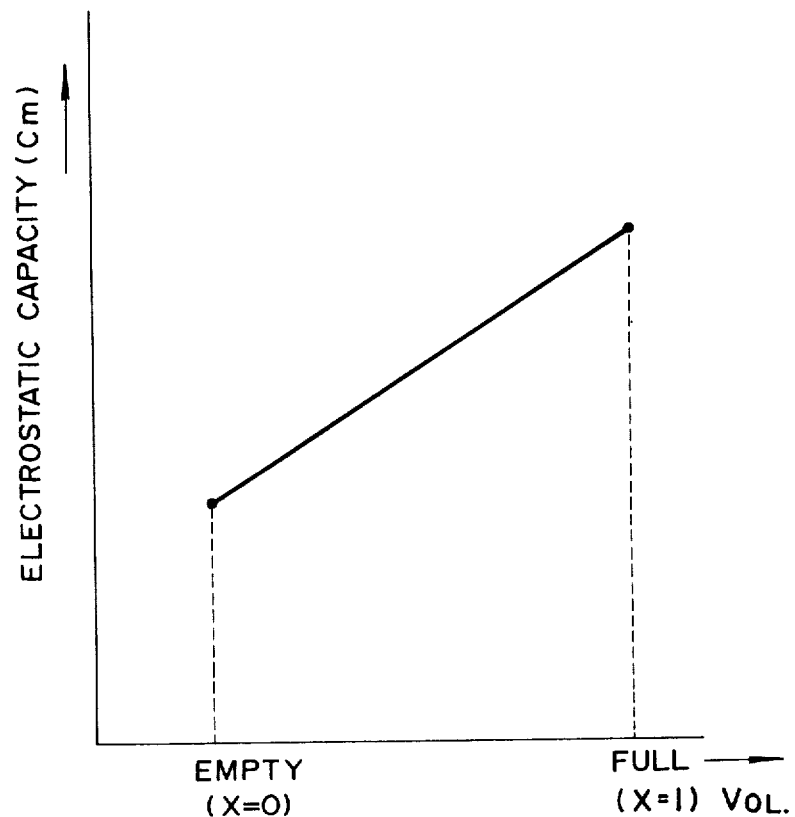
FIG. 6 is a graph showing the amount of fuel or other liquid medium contained in the fuel tank as a function of electrostatic capacity.

It should be noted that the measuring electrodes 2 are preferably shaped so that x is such that the capacitance produced is in fact proportional to the amount of fuel in the tank. That is to say, be shaped so that the capacitance decreases with the reduction in fuel volume as shown in FIG. 6.

From the foregoing it will be obvious that as the dielectric constant of the fuel $(E_f)$ can be determined using equation (1), then irrespective of the kind of fuel, the amount of water removing agent (if any) the temperature etc, by using the dielectric constant as derived above and the capacitance $(C_m)$ developed by the measuring electrodes in equation (2), an accurate calculation of the amount of fuel actually contained in the tank may be performed.

Apart from permitting an accurate determination of the amount of fuel in the tank, the arrangement disclosed hereinbefore may also be used to determine the amount of impurities, such as water, or additives contained in the fuel. This is possible as the fuel which is pumped between the electrodes 34 firstly passes through two filters and the pump before actually coming into contact with the reference electrodes per se, whereby the water (by way of example) is broken up into small droplets which only temporarily adhere to the electrodes and are then subsequently removed. Accordingly, as the dielectric constant of water is about 40 times that of gasoline and ethanol and methanol 12 and 15 times that of alcohol respectively, upon impingement of a droplet of water or alcohol for example, on the electrodes, the capacitance developed by the electrodes fluctuates depending on the amount and type of impurity, whereby it is possible to apply the output of the reference electrodes to a discriminating circuit which senses, via the capacitance fluctuation, the amount and type of impurity contained in the fuel.

Figure 7:
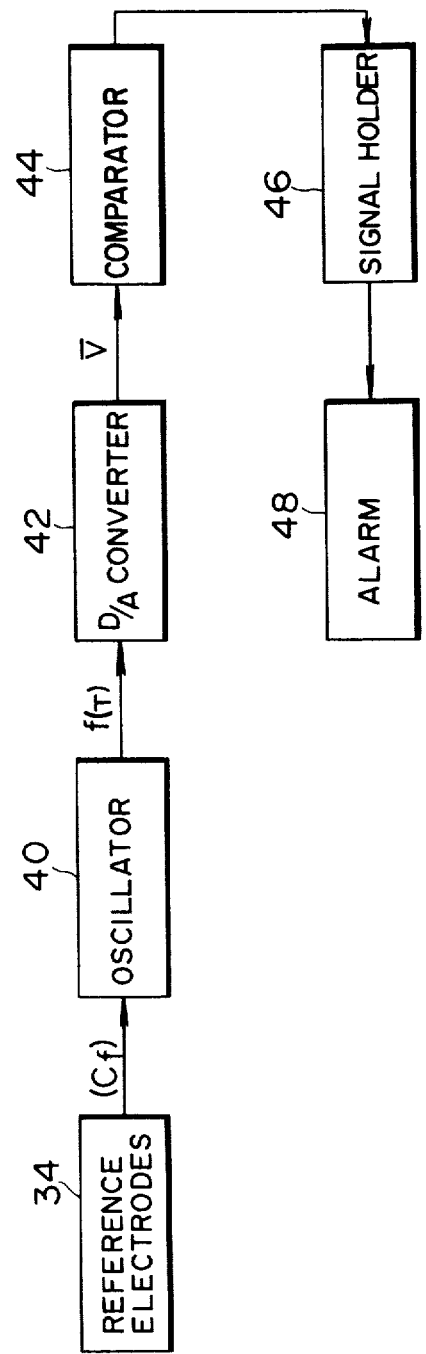
FIG. 7 is a block diagram showing circuitry which may be utilized in conjunction with the arrangement shown in FIG. 1 for detecting the type and amount of impurity which might be contained in the fuel.

An example of the abovementioned circuit is shown in FIG. 7. In this arrangement, the output of the reference electrodes 34 is applied to an oscillator 40 which, via frequency or period conversion outputs a digital signal f(T). This signal is fed to a digital analog (D/A) converter 42 which produces a voltage signal V which is fed to a comparator 44. The comparator 44 compares this voltage with a reference and upon the input exceeding the reference level, outputs a signal to a signal holder 46 which, if maintained in a predetermined state for more than a predetermined amount of time, tiggers an alarm 48. Hence, if the amount of water contained in gasoline type fuel exceeds a desirable value, or a "gasohol" type fuel seperates into layers wherein the lower layer is rich in alcohol and the upper layer rich in gasoline, the circuit connected to the reference electrodes will generate a signal indicative of same.

A further merit of the afore disclosed arrangement comes in that the pump 8 is located in the cool environment of the fuel tank and not in close proximity to a relatively hot engine. This is particularly advantageous in preventing "vapor lock" which is apt to occur especially with "gasohol" type fuels.

What is claimed is:

1. An apparatus for measuring the level of a liquid medium contained in a tank, comprising:
   a set of measuring electrodes immersed in said liquid medium for developing a capacitance which varies with the amount of liquid medium in said tank;
   a pump disposed within said tank;
   means defining a chamber into which said pump discharges said liquid medium, said chamber being adapted to be totally filled by the discharge of said pump;
   a plurality of parallel reference electrodes which are disposed in said chamber and arranged parallel to the direction that the liquid medium flows through said chamber and so that said liquid medium flows between said electrodes, said electrodes being arranged so that alternating electrodes are electrically connected for developing a capacitance which varies with the dielectric constant of said liquid medium flowing through said chamber; and
   circuit means associated with said measuring electrodes and said reference electrodes for producing a signal indicative of the amount of liquid medium in said tank.

2. An apparatus as claimed in claim 1, further comprising a filter through which said liquid medium must pass, said filter comprising a porous synthetic resin which is disposed in said chamber and adapted to support said reference electrodes thereon.

3. An apparatus as claimed in claim 1, wherein said circuit means further includes discriminating circuit means responsive to the capacitance developed by said reference electrodes for detecting the presence of and discriminating among different types of foreign matter in said liquid medium and for issuing an alarm upon an excess of said foreign matter being detected.

4. An apparatus as claimed in claim 3, wherein said discriminating circuit means comprises:
   an oscillator connected to said reference electrodes for converting the output of said reference electrodes into a digital signal by variation of frequency and period of the output received from said reference electrodes;
   a digital/analog converter means connected to receive said digital signal and for outputting a voltage signal corresponding thereto;
   a comparator means connected to said digital/analog converter means for receiving said voltage signal and comparing some with a reference voltage;
   a signal holder means operatively connected to said comparator for outputting a signal if the comparator produces an output for a predetermined period of time; and
   an alarm unit which is responsive to the output from said signal holder means for producing an alarm.

5. An apparatus as claimed in claim 1, further comprising a pressure regulating valve interposed between said chamber and said pump.

6. An apparatus as claimed in claim 1, further comprising a filter disposed upstream of said pump and through which said liquid medium must flow before entering said pump.

7. An apparatus as claimed in claim 6, further comprising means for discharging bubbles or the like upstream of said filter to a level defined above the surface of said liquid medium.

8. In an apparatus for measuring the level of a liquid medium in a tank
 a set of measuring electrodes immersed in said liquid medium for developing a capacitance which varies with the amount of liquid medium in said tank;
 a pump disposed within said tank;
 means defining a chamber into which said pump discharges said liquid medium, said chamber being adapted to be totally filled by the discharge of said pump;
 a plurality of reference electrodes disposed in said chamber, said electrodes being arranged so that the liquid medium flows therebetween to develop a capacitance which varies with the dielectric constant of said liquid medium flowing through said chamber;
 means upstream of said chamber for dispersing impurities in said liquid medium prior to passing through said chamber; and
 circuit means responsive to the output of said reference and measuring electrodes for indicating the amount of liquid medium in said tank and the constitution thereof.

9. An apparatus for measuring the level of a liquid medium contained in a tank, comprising:
 a set of measuring electrodes immersed in said liquid medium for developing a capacitance which varies with the amount of liquid medium in said tank;
 a pump disposed within said tank;
 means defining a chamber into which said pump discharges said liquid medium, said chamber being adapted to be totally filled by the discharge of said pump;
 a plurality of parallel planar reference electrodes spaced apart from each other, disposed in said chamber and arranged parallel to a direction of flow of the liquid medium so that said liquid medium flows in spaces provided between said electrodes, said electrodes being directly exposed to said liquid medium and in direct contact therewith, so that a capacitance developed between said electrodes in accordance with the dielectric constant of said liquid medium therebetween flowing through said chamber; and
 circuit means associated with said measuring electrodes and said reference electrodes for producing a signal indicative of the amount of liquid medium in said tank.

10. An apparatus as recited in claim 9 further comprising:
 means defining a chamber within said tank into which said pump discharges;
 first filter means upstream of said reference electrodes, arranged within said chamber for supporting said reference electrodes thereon,
 second filter means disposed upstream of said pump, and
 means disposed upstream of said pump for discharging bubbles or the like.

11. An apparatus as recited in claim 10 wherein said means defining a chamber comprises a bell-shaped structure for housing said plurality of reference electrodes, and including said first filter in a structure forming a base for said bell-shaped structure to provide said chamber.

* * * * *